US008597662B2

(12) United States Patent
Jacobs et al.

(10) Patent No.: US 8,597,662 B2
(45) Date of Patent: Dec. 3, 2013

(54) **VACCINE FOR PROTECTION AGAINST *LAWSONIA INTRACELLULARIS***

(71) Applicant: Intervet International B.V.

(72) Inventors: Antonius Arnoldus Christiaan Jacobs, Boxmeer (NL); Paul Vermeij, Boxmeer (NL); Ruud Philip Antoon Maria Segers, Boxmeer (NL); Carla Christina Schrier, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 13/657,210

(22) Filed: Oct. 22, 2012

(65) Prior Publication Data

US 2013/0045228 A1    Feb. 21, 2013

Related U.S. Application Data

(62) Division of application No. 12/988,083, filed as application No. PCT/EP2009/054516 on Apr. 16, 2009, now abandoned.

(60) Provisional application No. 61/046,161, filed on Apr. 18, 2008, provisional application No. 61/111,756, filed on Nov. 6, 2008.

(30) Foreign Application Priority Data

Apr. 18, 2008   (EP) .................................... 08154764
Nov. 6, 2009    (EP) .................................... 08105738

(51) Int. Cl.
  *A61K 39/02*     (2006.01)
  *C12N 1/20*      (2006.01)
(52) U.S. Cl.
  USPC .................. 424/234.1; 424/184.1; 435/252.1
(58) Field of Classification Search
  None
  See application file for complete search history.

(56) References Cited

U.S. PATENT DOCUMENTS

| 6,921,536 B2 | 7/2005 | Jacobs et al. |
| 2007/0014815 A1 | 1/2007 | Kroll et al. |
| 2007/0212373 A1 | 9/2007 | Vermeij |

FOREIGN PATENT DOCUMENTS

| EP | 382271 B1 | 12/1994 |
| EP | 843818 B1 | 2/2005 |
| EP | 1219711 B1 | 6/2006 |
| WO | 97/20050 A1 | 6/1997 |
| WO | 00/69906 A1 | 11/2000 |
| WO | 02/26250 A2 | 4/2002 |
| WO | 2005/011731 A1 | 2/2005 |
| WO | 2005/070958 A2 | 8/2005 |
| WO | 2006/099561 A1 | 9/2006 |
| WO | 2007/028823 A1 | 3/2007 |
| WO | 2007/103042 A2 | 9/2007 |
| WO | 2007/140244 A2 | 12/2007 |

OTHER PUBLICATIONS

Haesebrouck et al, "Efficacy of Vaccines Against Bacterial Diseases in Swine: What Can We Expect?", Veterinary Microbiology, vol. 100, pp. 255-268 (2004).
Hyland et al, "Oral Immunization Induces Local and Distant Mucosal Immunity in Swine", Veterinary Immunology and Immunopathology, vol. 102, pp. 329-338 (2004).
Kroll et al, "Lipopolysaccharide-Based Enzyme-Linked Immunosorbent Assay for Experimental Use in Detection of Antibodies to *Lawsonia intracellularis* in Pigs", Clinical and Diagnostic Laboratory Immunology, vol. 12, No. 6, pp. 693-699 (2005).
International Search Report in corresponding PCT/EP2009/054516, mailed Mar. 8, 2010.
International Search Report in corresponding PCT/EP2009/054517, mailed Aug. 5, 2010.

*Primary Examiner* — Padma V Baskar

(57) ABSTRACT

The present invention pertains to the use of a non-live carbohydrate containing composition, the carbohydrate being also found in live *Lawsonia intracellularis* cells in association with the outer cell membrane of these cells, for the manufacture of a vaccine for protection against an infection with *Lawsonia intracellularis*, the vaccine being in a form suitable for systemic administration.

3 Claims, No Drawings

VACCINE FOR PROTECTION AGAINST LAWSONIA INTRACELLULARIS

CROSS-REFERENCE TO RELATED APPLICATIONS

This application is a divisional application of U.S. application Ser. No. 12/988,083, filed Oct. 15, 2010, which is the National filing under 35 U.S.C. §371 of PCT/EP2009/054516, filed Apr. 16, 2009, which claims priority under 35 U.S.C. 119(e) to U.S. provisional Application No. 61/046, 161, filed Apr. 18, 2008 and U.S. provisional Application No. 61/111,756 filed Nov. 6, 2008, and claims foreign priority under 35 U.S.C. §119(a) to European Application No. 08154764.8, filed Apr. 18, 2008, and European Application No. 081054738.2, filed Nov. 6, 2008. The contents of PCT/EP2009/054516 and U.S. application Ser. No. 12/988,083 are hereby incorporated by reference in their entireties.

The present invention pertains to a vaccine for protection against an infection with *Lawsonia intracellularis*, a vaccine in this sense being a composition that at least provides a decrease in a negative influence of the infection with *Lawsonia intracellularis*, such negative influence being e.g. tissue damage and/or clincal signs such as decreased weight gain, diarrhea, etc.

Proliferative enteropathy (also called enteritis or ileitis) in many animals, in particular pigs, presents a clinical sign and pathological syndrome with mucosal hyperplasia of immature crypt epithelial cells, primarily in the terminal ileum. Other sites of the intestines that can be affected include the jejunum, caecum and colon. Weanling and young adult pigs are principally affected with typical clinical manifestation of rapid weight loss and dehydration. Natural clinical disease in pigs occurs worldwide. The disease is consistently associated with the presence of intracellular curved bacteria, presently known as *Lawsonia intracellularis*.

In general, oral vaccination against *Lawsonia intracellularis* has shown to be an economically efficient measure to control Ileitis and to allow a better exploitation of the genetic growth potential of the pig (Porcine Proliferative Enteropathy Technical manual 3.0, July 2006; available from Boehringer Ingelheim). Furthermore, oral rather than parenteral vaccination will reduce the transmission of blood-borne infections such as PRRS via multi-use needles and the reduction of injection site reactions and needles retained in carcasses. It will reduce animal and human stresses, time, labour costs and effort compared to individual vaccination (McOrist: "Ileitis—One Pathogen, Several Diseases" at the IPVS Ileitis Symposium in Hamburg, Jun. 2, 2004).

It is generally understood that the advantage of an attenuated live vaccine approach is that the efficacy of immunity is usually relatively good, as the host's immune system is exposed to all the antigenic properties of the organism in a more "natural" manner. Specifically for intracellular bacterial agents such as *Lawsonia intracellularis*, the live attenuated vaccine approach is believed to offer the best available protection for vaccinated animals, due to a full and appropriate T cell based immune response. This is in contrast with the variable to poor immunity associated with subunit or killed vaccine types for intracellular bacteria. This is also specifically true for obligate intracellular bacteria such as *Lawsonia intracellularis* or the *Chlamydia* sp, which cause pathogenic infections within the mucosa. Studies indicate that whole live attenuated forms of the intracellular bacteria in question are best delivered to the target mucosa, that they are required as whole live bacterial forms to produce a fully protective immune response in the target mucosa but also that they are immunologically superior compared to use of partial bacterial components.

It has become a general understanding that a vaccine against *Lawsonia intracellularis* needs to be administered orally (see i.a. Technical Manual 3.0 as referred to here-above). This is based on the fact that the basis of the body's resistance to Ileitis is the local immunity in the intestine, which is the product of cell-mediated immunity and local defense via antibodies, especially IgA. According to current knowledge, serum antibodies (IgG) do not give any protection simply because they do not reach the gut lumen. It has been demonstrated in studies that oral vaccination produces cell-mediated immunity as well as local production of IgA in the intestine (Murtaugh, in Agrar- and Veterinär-Akademie, Nutztierpraxis Aktuell, Ausgabe 9, Juni 2004; and Hyland et al. in Veterinary Immunology and Immunopathology 102 (2004) 329-338). In contrast, intramuscular administration did not lead to protection. Moreover, next to the general understanding that a successful vaccine against intracellular bacteria has to induce cell-mediated immunity as well as the production of local antibodies, the skilled practitioner knows that only a very low percentage of orally ingested antigens are actually absorbed by the enterocytes, and that the incorporation of *Lawsonia intracellularis* into the cell is an active process initiated by the bacterium. Accordingly an inactivated vaccine would provide the intestine with insufficient immunogenic antigen (Haesebrouck et al. in Veterinary Microbiology 100 (2004) 255-268). This is why it is believed that only attenuated live vaccines induce sufficient cell-mediated protection in the intestinal cells (see Technical Manual 3.0 as referred to here-above). At present there is only one vaccine on the market to protect against *Lawsonia intracellularis*, viz. Enterisol ® Ileitis marketed by Boehringer Ingelheim. This vaccine is a live vaccine for oral administration indeed.

It is an object of the present invention to provide an alternative vaccine to protect against an infection with *Lawsonia intracellularis*. To this end it has been devised to use a non-live carbohydrate containing composition, the carbohydrate being also found in live *Lawsonia intracellularis* ells in association with the outer cell membrane of these cells, for the manufacture of a vaccine for protection against an infection with *Lawsonia intracellularis*, the vaccine being in a form suitable for systemic administration. Surprisingly, against the persistent general understanding how to combat *Lawsonia intracellularis*, it was found that by using a carbohydrate containing non-live composition, for example extracted from the outer cell membrane of *Lawsonia intracellularis*, as an antigen in a vaccine, one can induce a protection against *Lawsonia intracellularis* that is comparable with or even improved with respect to the protection provided by using the live vaccine Enterisol® Ileitis (administered according to the corresponding instructions), when the antigen is administered systemically, i.e. in a way that it reaches the circulatory system of the body (comprising the cardiovascular and lymphatic system), thus affecting the body as a whole rather than a specific locus such as the gastro-intestinal tract. Systemic administration can be performed e.g. by administering the antigens into muscle tissue (intramuscular), into the dermis (intradermal), underneath the skin (subcutaneous), underneath the mucosa (submucosal), in the veins (intravenous) etc. Apart from the very good protection obtainable, an important advantage of the present non-live vaccine is that it is an inherent safety when compared to a live vaccine.

In general, the carbohydrate containing composition can be used to manufacture a vaccine by using art-known methods that basically comprise admixing the antigenic carbohydrate containing composition (or a composition derived therefrom, such as a dilution or concentrate of the original composition or an extract, one or more purified components etc.) with a pharmaceutically acceptable carrier, e.g. a liquid carrier such as (optionally buffered) water or a solid carrier such as commonly used to obtain freeze-dried vaccines. As such, manufacturing can take place in an industrial environment but also, the antigens could be mixed with the other vaccine constituents in situ (i.e. at a veterinaries', a farm etc.), e.g. (immediately) preceding the actual administration to an animal. In the vaccine, the antigens should be present in an immunologically effective amount, i.e. in an amount capable of stimulating the immune system of the target animal sufficiently to at least reduce the negative effects of a post-vaccination challenge with wild-type micro-organisms. Optionally other substances such as adjuvants, stabilisers, viscosity modifiers or other components are added depending on the intended use or required properties of the vaccine. For systemic vaccination many forms are suitable, in particular liquid formulations (with dissolved, emulsified or suspended antigens) but also solid formulations such as implants or an intermediate form such as a solid carrier for the antigen suspended in a liquid. Systemic vaccination, in particular parenteral vaccination (i.e. not trough the alimentary canal), and suitable (physical) forms of vaccines for systemic vaccination have been known for more than 200 years.

It is noted that subunits of *Lawsonia intracellularis* cells have been reported as antigens in a vaccine for protection against this bacterium. However, these are mainly recombinant proteins and hitherto none of them has proven to be able and provide good protection. Killed bacteria (which inherently contain the carbohydrate that is also found in live *Lawsonia intracellularis* cells in association with the outer cell membrane) are also suggested as antigens in vaccines against *Lawsonia intracellularis* but no vaccines based on killed whole cells have actually been tested and reported to provide good protection. Apart from that, systemic administration has not been used in conjunction with these killed bacteria, because of the general understanding that there is no reasonable expectation of success for systemic administration of antigens to locally (i.e. in the intestines) combat *Lawsonia intracellularis*.

In this respect it is noted that in WO 97/20050 (Daratech PTY Ltd) mentions the use of killed *Lawsonia intracellularis* bacteria to immunize pigs. However, systemic administration is not mentioned. Based on the current knowledge that vaccination is only effective upon oral administration, it is commonly understood that the oral route was the administration route chosen for the experiments described in the Daratech application. Another patent application that mentions killed bacteria is WO 2005/011731 (Boehringer Ingelheim). However, actually disclosed is only the use of a live vaccine administered orally. It is not shown that a killed vaccine may be effective, let alone that the killed vaccine can be given systemically. EP 843 818 (Boehringer Ingelheim) describes the intramuscular administration of a killed vaccine (paragraph [0115] in combination with paragraph [0119]). In par [0115] it is stated that the bacteria were killed by storing them at 4° C. at normal atmospheric conditions. As is commonly known however, under such conditions *Lawsonia intracellularis* bacteria survive. Thus, this document does not teach the subject matter of the present invention. It is also noted that a carbohydrate containing composition, wherein the carbohydrate is also found in live *Lawsonia intracellularis* cells in association with the outer cell membrane of these cells, is known from Kroll et al. (Clinical and Diagnostic Laboratory Immunology, June 2005, 693-699). However, this composition is used for diagnostics. It has not been tested as a protective antigen for reasons as stated here-above.

In an embodiment, the carbohydrate containing composition is material resulting from the killing of *Lawsonia intracellularis* bacteria. It has been found that a very convenient way of providing the carbohydrate for use according to the present invention is to simply kill *Lawsonia intracellularis* cells and use the material resulting from that as a source for the carbohydrate. To extract the carbohydrate from living cells could in theory also be done (analogous to the creation of living ghost cells by removing the cell wall) but requires more sophisticated and thus more expensive techniques. The material as a whole could be used, e.g. a suspension of whole cells or a lysate of *Lawsonia intracellularis* cells, or one could purify or even isolate the carbohydrate out of the material. This method can be performed by using relatively simple art-known techniques.

In a preferred embodiment the carbohydrate containing composition contains whole cells of killed *Lawsonia intracellularis* bacteria This has proven to be the most convenient way to provide the carbohydrate as an antigen in the vaccine. Besides, the efficacy of the vaccine is even further increased, possibly since this way of offering the antigen to the immune system of the target animal better mimics the natural environment of the carbohydrate.

In an embodiment the vaccine comprises an oil in water adjuvant containing oil droplets of sub-micrometer size. In general, an adjuvant is a non-specific immunostimulating agent. In principal, each substance that is able to favor or amplify a particular process in the cascade of immunological events, ultimately leading to a better immunological response (i.e. the integrated bodily response to an antigen, in particular one mediated by lymphocytes and typically involving recognition of antigens by specific antibodies or previously sensitized lymphocytes), can be defined as an adjuvant. It has been shown that using an oil in water adjuvant containing oil droplets of sub-micrometer size provides a very good protection against *Lawsonia intracellularis*. Indeed, the application of oil in water adjuvants as such is common in connection with non-live antigens. However, it is generally known that the best immunostimulating properties are obtained when the oil droplets are large in diameter. In particular, oil droplets with a diameter beneath 1 micrometer are in particular used when it is believed that safety is an important issue. In that case, one could use small droplets since these are known to evoke less tissue damage, clinical signs etc. However, in the case of obtaining protection for a gut associated disorder via systemic vaccination (as is the case in the present invention), one would choose large droplets since one would expect that the immune response has to be boosted significantly. In contrast, we found that using small oil droplets in the composition provided very good results with respect to protection against *Lawsonia intracellularis*.

In an even preferred embodiment, the adjuvant comprises droplets of biodegradable oil and droplets of mineral oil, the droplets of biodegradable oil having an average size that differs from the average size of the droplets of mineral oil. It has been shown that the use of a mixture of biodegradable oil and mineral oil provides very good results with regard to efficacy and safety. In addition to this, stability of the composition is very high, which is an important economic advantage. The stability has proven to be very good, in particular when the average (volume weighed) size of either the biodegradable oil droplets or the mineral droplets is below 500 nm (preferably around 400 nm).

In an embodiment, the vaccine further comprises antigens of *Mycoplasma hyopneumoniae* and Porcine circo virus. Hitherto combination vaccines of *Lawsonia intracellularis* have been suggested in the prior art. However, not many of such combinations have actually been tested for efficacy. The reason for this is that it is generally understood that combination of antigens with antigens of *Lawsonia intracellularis* can only lead to successful protection if the *Lawsonia* antigens are provided as live (attenuated) cells. In this respect, we refer to WO 2005/011731, which also suggests all kinds of combination vaccines based on *Lawsonia intracellularis*. However, regarding the description and claim structure the patent application, the assignee (Boehringer Ingelheim) appears to be convinced that combination vaccines are only expected to have a reasonable chance of success when the *Lawsonia* antigens are present in the form of live cells. The same is true for WO 2006/099561, also assigned to Boehringer Ingelheim. Indeed, based on the common general knowledge this is an obvious thought.

The invention will be further explained using the following examples.

Example 1 describes a method to obtain a substantially protein free carbohydrate containing composition and a vaccine that is made by using this composition.

Example 2 describes an experiment wherein a second vaccine according to the present invention is compared with the vaccine currently on the market and an experimental vaccine comprising subunit proteins of *Lawsonia intracellularis*.

Example 3 describes an experiment wherein two different vaccines according to the present invention are compared with the vaccine currently on the market.

Example 4 describes an experiment wherein a dosage affect of a vaccine according to the invention is established.

EXAMPLE 1

In this example a method is described to obtain a substantially protein free carbohydrate composition associated with the outer cell membrane of *Lawsonia intracellularis* cells and a vaccine that can be made using this composition. In general, a carbohydrate is an organic compound that contains carbon, hydrogen, and oxygen, usually in the ratio 1:2:1. Examples of carbohydrates are sugars (saccharides), starches, celluloses, and gums. Usually they serve as a major energy source in the diet of animals. *Lawsonia intracellularis* is a gram negative bacterium, which thus contains an outer membrane that is not constructed solely of phospholipid and protein, but also contains carbohydrates, in particular polysaccharide (usually polysaccharides such as lipopolysaccharide, lipo-oligosaccharde, or even non-lipo polysaccharides).

Carbohydrate Fraction for Vaccine Preparation

Twenty milliliters of buffered water (0.04 M PBS, phosphate buffered saline) containing *Lawsonia intracellularis* cells at a concentration of $3.7E8$ ($=3.7 \times 10^8$) cells/ml was taken. The cells were lysed by keeping them at 100° C. for 10 minutes. Proteinase K (10 mg/ml) in 0.04 M PBS was added to a final concentration of 1.7 mg/ml. This mixture was incubated at 60° C. for 60 minutes in order to degrade all proteins and keep the carbohydrates intact. Subsequently, the mixture was incubated at 100° C. for 10 minutes to inactivate the Proteinase K. The resulting material, which is a carbohydrate containing composition, in particular containing the carbohydrates as present in live *Lawsonia intracellularis* bacteria in association with their outer cell membrane (see paragraph below), was stored at 2-8° C. until further use. The composition was formulated in Diluvac forte adjuvant. This adjuvant (see also EP 0 382 271) comprises 7.5 weight percent vitamine E acetate droplets with an average volume weighted size of approximately 400 nm, suspended in water and stabilized with 0.5 weight percent of Tween 80 (polyoxyethylene sorbitan mono-oleate). Each milliliter vaccine contained material that had been extracted from $1.2E8$ *Lawsonia intracellularis* cells.

Immune Precipitation of *Lawsonia* Carbohydrate Antigens

Two batches of monoclonal antibodies (MoAb's) raised against whole cell *Lawsonia intracellularis* were precipitated with saturated $Na_2SO_4$ at room temperature according to standard procedures. The precipitate was pelleted by centrifugation (10.000 g for 10 minutes). The pellet was washed with 20% $Na_2SO_4$ and resuspended in 0.04 M PBS. Tylosyl activated Dynal beads (DynaBeads, DK) were pre washed with 0.1 M $NaPO_4$ (pH 7.4), according the manual of the manufacturer. Of each batch of MoAb's 140 µg was taken and added to 2E8 pre washed beads and incubated overnight at 37° C. The beads were pelleted by centrifugation and non-bound MoAb's were removed by aspiration of the supernatant. Spectrophotometrical measurements showed that between 20 and 35% of the added MoAb's had bound to the beads.

Two batches of 1 ml *Lawsonia intracellularis* cells (3.7E8/ml) in 0.04 M PBS were sonicated for 1 minute. The resulting cell lysates were added to the Tylosyl activated beads—monoclonal complexes and incubated overnight at 4° C. The Tylosyl activated beads—monoclonal complexes were washed three times with 0.1 M $NaPO_4$ (pH 7.4). The bound compounds were eluted by washing the beads in 0.5 ml 8M urea in 0.04 M PBS (E1); 0.5 ml 10 mM Glycine pH 2.5 (E2); and 0.5 ml 50 mM HCI (E3), in a sequential manner. After elution E2 and E3 were neutralized with either 100 µl and 200 µl 1 M Tris/HCI (pH8.0).

Samples were taken from each step and loaded onto SDS-PAGE gels. Gels were stained using Commassie Brilliant Blue (CBB) and Silver staining or blotted. The blots were developed using the same MoAb's as mentioned here-above. Inspection of the gels and blots showed that the MoAb's recognized bands with an apparent molecular weight of 21 and 24 kDa that were not seen on the CBB gels but were visible on de Silver stained gels. Also, it was established that the fraction of the cells that bound to the MoAb's was Proteinase K resistant. Thus, based on these results it can be concluded that this fraction contains carbohydrates (namely: all protein is lysed, and sonified DNA fractions will not show as a clear band in a Silver stain), and that the carbohydrates are in association with (i.e. forming part of or being bound to) the outer cell membrane of *Lawsonia intracellularis* (namely: the MoAb's raised against this fraction also recognized whole *Lawsonia intracellularis* cells). Given the fact that *Lawsonia intracellularis* is a gram-negative bacterium, the carbohydrate composition is believed to comprise polysaccharide(s).

EXAMPLE 2

This experiment was conducted to test a convenient way to formulate the carbohydrate antigen in a vaccine, viz. via a killed whole cell (also known as bacterin). As controls the commercially available vaccine Enterisol® ileitis and an experimental subunit vaccine comprising protein subunits were used. Next to this unvaccinated animals were used as a control.

Experimental Design of Example 2

An inactivated whole cell vaccine was made as follows. Live *Lawsonia intracellularis* cells derived from the intestines of pigs with PPE were gathered. The cells were inactivated with 0.01% BPL (beta-propiolactone). The resulting material, which inherently is a non-live carbohydrate containing composition in the sense of the present invention (in particular since it contains the carbohydrates as present in live *Lawsonia intracellularis* bacteria in association with their outer cell membrane), was formulated in Diluvac forte adjuvant (see Example 1) at a concentration of approximately $2.8 \times 10^8$ cells per ml vaccine.

The subunit vaccine contained recombinant P1/2 and P4 as known from EP 1219711 (the 19/21 and 37 kDa proteins respectively), and the recombinant proteins expressed by genes 5074, 4320 and 5464 as described in WO2005/070958. The proteins were formulated in Diluvac forte adjuvant. The vaccine contained approximately 50 μgrams of each proteins per milliliter.

Forty 6-week-old SPF pigs were used. The pigs were allotted to 4 groups of ten pigs each. Group 1 was vaccinated once orally (at T=0) with 2 ml live "Enterisol® ileitis" (Boehringer Ingelheim) according to the instructions of the manufacturer. Group 2 and 3 were vaccinated twice intramuscularly (at T=0 and T=4 w) with 2 ml of the inactivated *Lawsonia* whole cell vaccine and the recombinant subunit combination vaccine as described here-above, respectively. Group 4 was left as unvaccinated control. At T=6 w all pigs were challenged orally with homogenized mucosa infected with *Lawsonia intracellularis*. Subsequently all pigs were daily observed for clinical signs of Porcine Proliferative Enteropathy (PPE). At regular times before and after challenge serum blood (for serology) and faeces (for PCR) were sampled from the pigs. At T=9 w all pigs were euthanized and necropsied. Histological samples of the ileum were taken and examined microscopically.

The challenge inoculum was prepared from infected mucosa: 500 grams of infected mucosa (scraped from infected intestines) were mixed with 500 ml physiological salt solution. This mixture was homogenized in an omnimixer for one minute at full speed on ice. All pigs were challenged orally with 20 ml challenge inoculum at T=6 w.

At T=0, 4, 6, 7, 8 and 9 w a faeces sample (gram quantities) and a serum blood sample of each pig was taken and stored frozen until testing. The faeces samples were tested in a quantitative PCR (Q-PCR) test and expressed as the logarithm of the amount found in picograms (pg). Serum samples were tested in the commonly applied IFT test (immuno fluorescent antibody test to detect antibodies against whole *Lawsonia intracellularis* cells in the serum). For histological scoring a relevant sample of the ileum was taken, fixed in 4% buffered formalin, routinely embedded and cut into slides. These slides were stained with Hematoxylin-Eosin (HE stain) and with an immunohistochemical stain using anti-*Lawsonia intracellularis* monoclonal antobodies (IHC stain). The slides were examined microscopically. The histology scores are as follows:

| HE stain: | |
| --- | --- |
| no abnormalities detected | score = 0 |
| doubtful lesion | score = ½ |
| mild lesions | score = 1 |
| moderate lesions | score = 2 |
| severe lesions | score = 3 |
| IHC stain: | |
| no *L. intracelluaris* bacteria evident | score = 0 |
| doubtful presence of bacteria | score = ½ |
| presence of single/small numbers of bacteria in the slide | score = 1 |
| presence of moderate numbers of bacteria in the slide | score = 2 |
| presence of large numbers of bacteria in the slide | score = 3 |

All data were recorded for each pig individually. The score per group was calculated as the mean of the positive animals for the different parameters after challenge. The non-parametric Mann-Whitney U test was used to evaluate the statistical significance (tested two-sided and level of significance set at 0.05).

Results of Example 2

Serology

Before first vaccination all pigs were seronegative when tested for IFT antibody titres. After vaccination with the whole cell bacterin (group 2) pigs developed high IFT antibody titres whereas the controls and the pigs vaccinated with the subunit vaccine remained negative until challenge (Table 1). Two of the Enterisol® vaccinated pigs (group 1) developed moderate IFT titres whereas all other pigs in this group remained seronegative. After challenge all pigs developed high IFT antibody titers. Mean results are depicted in table 1 (with the used dilution, 1.0 was the detection level on the lower side).

TABLE 1

Mean IFT antibody titres (2log) of pig serum after vaccination and challenge

| Group | T = 0 weeks | T = 4 weeks | T = 6 weeks | T = 9 weeks |
| --- | --- | --- | --- | --- |
| 1 | <1.0 | 1.1 | 1.7 | >11.4 |
| 2 | <1.0 | 3.7 | >11.8 | >12.0 |
| 3 | <1.0 | <1.0 | <1.0 | >11.6 |
| 4 | <1.0 | <1.0 | <1.0 | >12.0 |

Real-time PCR on Faeces Samples

Before challenge all faeces samples were negative. After challenge positive reactions were found in all groups. Group 1 (p=0.02), group 2 (p=0.01) and group 3 (p=0.03) had a significantly lower shedding level compared to the control. A post-challenge overview is given in table 2.

TABLE 2

Mean results of PCR on faeces samples (log pg) after vaccination and challenge

| Group | T = 6 weeks | T = 7 weeks | T = 8 weeks | T = 9 weeks | Total post-challenge |
| --- | --- | --- | --- | --- | --- |
| 1 | 0 | 1.3 | 3.6 | 1.8 | 6.3 |
| 2 | 0 | 0.8 | 2.8 | 1.9 | 5.5 |
| 3 | 0 | 0.5 | 3.8 | 2.0 | 5.9 |
| 4 | 0 | 0.8 | 4.9 | 4.9 | 10.0 |

Histology Scores

Group 2 had the lowest histology HE score (p=0.05), IHC score (p=0.08) and total histology score (p=0.08). The other groups had higher scores and were not significantly different from the control group. See table 3.

TABLE 3

Mean histology score for the ileum.

| Group | HE score | IHC score | Total score |
|---|---|---|---|
| 1 | 1.8 | 1.5 | 3.3 |
| 2 | 1.3 | 1.5 | 2.7 |
| 3 | 1.8 | 1.6 | 3.4 |
| 4 | 2.4 | 2.3 | 4.7 |

Conclusion with Regard to Example 2

From the results it can be concluded that systemic administration of the non-live whole cell *Lawsonia intracellularis* vaccine which inherently contains the carbohydrate as found also in association with the outer membrane of live *Lawsonia intracellularis* cells, induced at least partial protection. All parameters studied and histology scores were significantly or nearly significantly better compared to the controls.

EXAMPLE 3

This experiment was conducted to test a vaccine comprising a carbohydrate containing composition as antigen. A second vaccine to be tested contained in addition to killed whole cells of *Lawsonia intracellularis*, antigens of *Mycoplasma hyopneumoniae* and Porcine circo virus (the "combi" vaccine). As a control the commercially available Enterisol® ileitis vaccine was used. Next to this, unvaccinated animals were used as a second control.

Experimental Design of Example 3

The vaccine based on a substantially protein free carbohydrate containing composition was obtained as described under Example 1.

The experimental combi vaccine contained inactivated *Lawsonia intracellularis* whole cell antigen (see Example 2 for the used method of providing the inactivated bacteria) at a level of 1.7×10⁸ cells/ml. Next to this it contained inactivated PCV-2 antigen (20 µgrams of the ORF 2 encoded protein of PCV 2 per ml; the protein being expressed in a baculo virus expression system as commonly known in the art, e.g. as described in WO 2007/028823) and inactivated *Mycoplasma hyopneumoniae* antigen (the same antigen in the same dose as is known from the commercially available vaccine Porcilis Mhyo®, obtainable from Intervet, Boxmeer, The Netherlands). The antigens were formulated in a twin emulsion adjuvant "X". This adjuvant is a mixture of 5 volume parts of adjuvant "A" and 1 volume part of adjuvant "B". Adjuvant "A" consists of mineral oil droplets with an approximate average (volume weighed) size around 1 µm, stabilised with Tween 80 in water. Adjuvant "A" comprises 25 weight % of the mineral oil and 1 weight % of the Tween. Rest is water. Adjuvant "B" consists of droplets of biodegradable vitame E acetate with an approximate average (volume weighed) size of 400 nm, stabilised also with Tween 80. The adjuvant "B" comprises 15 weight % of vitamine E acetate and 6 weight % of Tween 80, rest is water.

Sixty-four 3-day-old SPF piglets were used. The pigs were allotted to four groups of 14 piglets and one group of 8 piglets (Group 4). Group 1 was vaccinated intramuscularly at 3 days of age with 2 ml of the combi vaccine, followed by a second vaccination at 25 days of age. Group 2 was vaccinated intramuscularly once with 2 ml combi vaccine at 25 days of age. Group 3 was vaccinated orally with 2 ml Enterisol® ileitis (Boehringer Ingelheim) at 25 days of age according to prescriptions. Group 4 was vaccinated intramusculary at 3 and 25 days of age with 2 ml of the non-protein carbohydrate vaccine. Group 5 was left unvaccinated as a challenge control group. At 46 days of age all pigs were challenged orally with homogenized infected mucosa. Subsequently all pigs were daily observed for clinical signs of Porcine Proliferative Enteropathy (PPE). At regular times before and after challenge serum blood and faeces samples were taken from the pigs for serology and PCR respectively. At 68 days of age all pigs were euthanized and post-mortem examined. The ileum was examined histologically.

The other issues in the experimental design were the same as described in Example 2, unless indicated otherwise.

Results of Example 3

Serology

Before first vaccination all pigs were seronegative for IFT *Lawsonia* antibody titres. After vaccination with the combi vaccine (groups 1 and 2) and the non-protein carbohydrate vaccine (group 4), many pigs developed IFT antibody titres whereas the controls and the pigs vaccinated with Enterisol remained seronegative until challenge. After challenge all pigs (except two in the Enterisol group) developed IFT antibody titres. For an overview of the mean values obtained, see table 4 (due to the higher dilution when compared to example 2, the detection level was 4.0).

TABLE 4

Mean IFT *Lawsonia* antibody titres (2log) of pig serum after vaccination and challenge

| Group | T = 3 days | T = 25 days | T = 46 days | T = 67 days |
|---|---|---|---|---|
| 1 | <4.0 | <4.0 | 7.9 | 10.3 |
| 2 | <4.0 | <4.0 | 4.8 | 9.8 |
| 3 | <4.0 | <4.0 | <4.0 | 8.5 |
| 4 | <4.0 | <4.0 | 6.9 | 10.6 |
| 5 | <4.0 | <4.0 | <4.0 | 9.0 |

With respect to Mhyo, at the start of the experiment as well as day of booster (25-day-old) all pigs were seronegative for Mhyo. After booster vaccination group 1 developed high Mhyo antibody titres, comparable to those obtained with the commercially available vaccine.

With respect to PCV, at 3-day-old the piglets had high maternally derived PCV antibody titres. At day of booster (25-day-old) the vaccinates (group 1) had a similar titre compared to group 2 and the control group. The PCV titre at 25-day-old was slightly lower compared to the titre at 3-day-old. After the vaccination at 25-day-old the titres of group 1 (2 vaccinations at day 3 and 25) and group 2 (one vaccination at day 25) remained at a high level whereas control piglets showed a normal decrease in maternally derived antibodies. The PCV titres obtained are comparable to the titres obtainable with commercially available vaccines.

Real-Time PCR on Faeces Samples Three weeks after challenge, pigs of group 1, 2 and 4 had less *Lawsonia* (DNA) in their feces compared to groups 3 and 5. Only the differences between group 1 and 3 (Enterisol) and group 4 and 3 were statistically significant (p<0.05, Mann-Whitney U test). For the mean results, see table 5.

TABLE 5

Mean results of PCR on faeces samples (log pg) after vaccination and challenge

| Group | Mean value |
|---|---|
| 1 | 1.0 |
| 2 | 1.2 |
| 3 | 2.0 |

TABLE 5-continued

Mean results of PCR on
faeces samples (log pg) after vaccination and challenge

| Group | Mean value |
|---|---|
| 4 | 0.6 |
| 5 | 1.8 |

Histological Scores

Histology scores of group 1 and 4 were significantly lower compared to those of groups 3 and 5 ($p<0.05$, two-sided Mann-Whitney U test (see table 6). The number of pigs with confirmed PPE were 2/13 in group 1, 6/12 in group 2, 12/14 in group 3, 2/7 in group 4 and 12/14 in the control group 5. Groups 1 and 4 had a significantly lower incidence of PPE compared to groups 3 and 5 ($p<0.05$, two-sided Fischers' exact test).

TABLE 6

Mean histology score for the ileum.

| Group | HE Score | IHC Score | Total Score |
|---|---|---|---|
| 1 | 0.4 | 0.6 | 1.0 |
| 2 | 0.7 | 0.7 | 1.4 |
| 3 | 1.6 | 1.4 | 3.0 |
| 4 | 0.4 | 0.4 | 0.8 |
| 5 | 1.9 | 1.5 | 3.4 |

Conclusion of Example 3

From the results it can be concluded that systemic administration of the whole cell *Lawsonia* bacterin combined with PCV and Mhyo antigen as well as the vaccine comprising (substantially protein-free) the carbohydrate, administered at 3-day-old and 25-day-old, both induce partial protection against experimental *Lawsonia intracellularis* infection. It is particularly surprising that the vaccine is effective when the prime administration takes place before weaning (younger than 21-25 days). It is noted that in the examples 2 and 3 the vaccines as far as *Lawsonia* antigens are concerned, per ml contain antigenic material derived from more than 1E8 *Lawsonia intracellucaris* cells. Given the fact that these vaccines, even though mild adjuvants are being used (viz. adjuvants containing small droplets and no or little mineral oil), confer good protection against ileitis, in particular when compared to the commercially available vaccine Enterisol® Ileitis, the dose of antigens could be lowered. This could be done by administering less vaccine (down to e.g. 0.2 ml, suitable for e.g. intradermal application), or decreasing the antigenic content of the vaccine. Based on analogues in vaccine technology it is believed that with an antigenic dose (per vaccination) derived from or containing 1E7 cells, in particular 2.5E7 cells or higher, still comparable or even better results can be obtained than with the current commercially available vaccine. Given the fact that the combination vaccine provided titres for Mhyo and PCV antibodies to a level comparable with the levels obtainable with commercially available single vaccines, it is understood that the combination vaccine also provides protection against *Mycoplasma hyopneumoniae* and Porcine circo virus.

EXAMPLE 4

This experiment was conducted to establish a dosage affect of a vaccine according to the invention. Also in this experiment unvaccinated animals were used as a control.

Experimental Design of Example 4

Inactivated whole cell vaccines were made as indicated in example 2. The antigenic material was formulated in Diluvac forte adjuvant at a concentration of approximately $2.0 \times 10^8$ cells per ml vaccine, respectively $5.0 \times 10^7$ and $1.25 \times 10^7$ cells per ml vaccine. Sixty 3-day-old SPF piglets were used. The pigs were allotted to four groups of 15 pigs each. The piglets of groups 1, 2 and 3 were vaccinated intramuscularly (in the neck) at 3-day old and 25-day-old with 2 ml of the vaccine each time. Group 4 was left as unvaccinated control. At 46-day-old all pigs were challenged orally with *Lawsonia* bacteria as indicated under example 2. At 67-day-old all pigs were euthanized and examined. Tests were performed as indicated under example 2. Next to this PCR was peformed on mucosa samples. For this, an ileum sample was taken from every animal, where applicable from an area which showed thickening.

Results of Example 4

Weight Gain

From 14 days and onwards significant differences in total weight gain appeared among the groups. Group 1 showed an average total weight gain of approximately 5350 grams. In group 2 this was 5150 grams. Group 3 showed a weight gain of about 4250 grams, whereas Group 4 showed a weight gain of 4550 grams.

Real-Time PCR on Faeces Samples

Three weeks after challenge positive reactions were found in all groups. Group 1 and Group 2 had a significantly lower shedding level compared to the control. A post-challenge overview of the number of infected animals (as determined by PCR) is given in table 7.

TABLE 7

Result of PCR on faeces samples after vaccination and challenge

| Group | Number of infected animals post-challenge |
|---|---|
| 1 | 1/15 |
| 2 | 2/15 |
| 3 | 7/15 |
| 4 | 8/15 |

Real-Time PCR on Mucosa Samples

Three weeks after challenge positive reactions were found in all groups. Group 1 and Group 2 had a significantly lower shedding level compared to the control. A post-challenge overview of the number of infected animals (as determined by PCR) is given in table 8.

TABLE 8

Result of PCR on mucosa samples after vaccination and challenge

| Group | Number of infected animals post-challenge |
|---|---|
| 1 | 0/15 |
| 2 | 2/15 |
| 3 | 5/15 |
| 4 | 6/14 (no sample of pig no 8) |

Histology Scores

The total histology score and the number of animals which were confirmed to have PPE are depicted in table 9.

TABLE 9

| Mean histology score for the ileum. | | |
|---|---|---|
| Group | Total score | Number of animals with PPE |
| 1 | 0.3 | 0/15 |
| 2 | 0.8 | 2/14 |
| 3 | 1.1 | 4/15 |
| 4 | 1.9 | 7/15 |

Conclusion of Example 4

Contrary to what was expected, the results indicate that there is a very sudden decrease in protective effect around the lowest dosage used in these experiments. Although a dosage of antigenic material derived from $2.5 \times 10^7$ cells still provided a protective effect comparable with that of the commercially available vaccine, the fact the decrease between a dosage that is only 0.6 log higher is so significant (hardly any effect seen in weight gain, number of infected animals and PCR on mucosa; however, still a decrease in number of PPE recognized animals), gave the insight that in general a practical lowest effective dose of the antigen can be derived at: an amount of antigens less than derived from or containing $1 \times 10^7$ cells will in practice, under the current market circumstances, not lead to economically relevant results. The reason for the existence of this apparent cut-off value is not 100% clear. Usually one expects a more gradual decrease in protection when the dosage is lowered. It might be that combating a local infection in the mucosa of the intestines via a systemically derived immune response needs a minimum amount of antigens.

Next to the above, the surprising effect seen in Example 3, viz. that a vaccine based on a carbohydrate antigen administered systemically, is effective when the prime administration takes place before weaning (younger than 21-25 days), is confirmed in this experiment with the use of another adjuvant. Therefore it can reasonably be understood that this feature is generic for a non-live vaccine comprising a carbohydrate antigen.

The invention claimed is:

1. A method of immunizing a piglet at 25 days of age or younger against *Lawsonia intracellularis* comprising systemically administering a single dose of a composition comprising non-live inactivated whole cell *Lawsonia intracellularis* bacteria at a concentration of more than or equal to $5.0 \times 10^7$ cells per ml.

2. The method according to claim 1, wherein the composition further comprises an oil in water adjuvant containing oil droplets of sub-micrometer size.

3. The method according to claim 2, wherein the adjuvant comprises droplets of biodegradable oil and droplets of mineral oil, the droplets of biodegradable oil having an average size that differs from the average size of the droplets of mineral oil.

* * * * *